United States Patent [19]

Thomas

[11] 3,931,250

[45] Jan. 6, 1976

[54] HETEROCYCLIC COMPOUND AS ODOR- AND FLAVOR-MODIFYING AGENT

[75] Inventor: Alan Francis Thomas, Geneva, Switzerland

[73] Assignee: Firmenich SA, Geneva, Switzerland

[22] Filed: Nov. 1, 1974

[21] Appl. No.: 520,154

[30] Foreign Application Priority Data

Nov. 2, 1973 Switzerland.................... 15424/73

[52] U.S. Cl. ............ 260/347.8; 252/522; 426/536; 260/347.4
[51] Int. Cl.² ...................................... C07D 307/34
[58] Field of Search ................................ 260/347.8

[56] References Cited
OTHER PUBLICATIONS

Sipma et al., Rec. Trav. Chim., Vol. 87, pp. 715–720 (1968).

*Primary Examiner*—Harry I. Moatz
*Attorney, Agent, or Firm*—Pennie & Edmonds

[57] ABSTRACT

New heterocyclic compound useful as odor-modifying agent for manufacturing perfumes, perfumed products, natural or synthetic essential oils, and as flavor-modifying agent for the manufacture of artificial flavors or for flavoring foodstuffs, animal feeds, beverages, pharmaceutical preparations and tobacco products.

Process for preparing said heterocyclic compound.

2 Claims, No Drawings

HETEROCYCLIC COMPOUND AS ODOR- AND FLAVOR-MODIFYING AGENT

SUMMARY OF THE INVENTION

The invention relates to a heterocyclic compound of formula

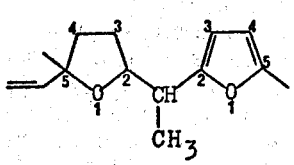

as well as to its use as odor- and flavor-modifying agent.

The invention also relates to a perfume or a flavor-modifying composition comprising as one of its active ingredients the compound of formula I as set forth hereinabove.

The invention finally relates to a process for the preparation of the compound of formula I, said process comprising A. condensing a compound of formula

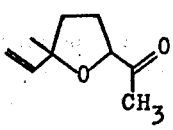

with a furan derivative of formula

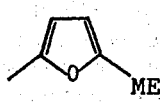

wherein the symbol ME represents an alkali metal, and

B. hydrolyzing the condensation product thus obtained to afford a compound of formula

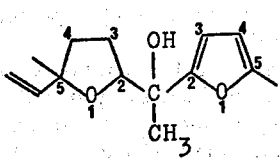

and subsequently reducing the said alcohol; or

B'. directly reducing the product resulting from the condensation described sub letter A.

BACKGROUND OF THE INVENTION

Compound I, defined as 1-(5-methyl-fur-2-yl)-1-(5-methyl-5-vinyl-tetrahydrofur-2-yl)-ethane, is a naturally occurring compound. It has been recently isolated as a trace component from Davana Oil (*Artemisia pallens*), by means of an expensive and rather complicated process. Said process included in fact several successive fractional distillations, followed by a series of preparative vapor phase chromatographies.

It was surprisingly discovered that, with respect to its organoleptic properties, 1-(5-methyl-fur-2-yl)-1-(5-methyl-5-vinyl-tetrahydrofur-2-yl)-ethane greatly differs from Davana oil. Compound I possesses in fact, in its pure state an original, fresh, green and somewhat fruity note, whereas Davana oil is described as possessing a sharp, penetrating, bitter-green, foliage-like and powerfully herbaceous odour [See S. Arctander, Perfumes and Flavor Chemicals, Montclair N.J. 1969, p. 212–3].

PREFERRED EMBODIMENTS OF THE INVENTION

In the field of perfumery 1-(5-methyl-fur-2-yl)-1-(5-methyl-5-vinyl-tetrahydrofur-2-yl)-ethane presents a well distinct, original, fresh and fruity olfactive note, reminiscent in most instances of that of black-current or that of lime for example. Compound I is therefore particularly suitable for preparing modern or classical perfume compositions, to which it imparts a pleasant fresh and fruity tonality. Compound I is also appreciated for the reconstruction of various essential oils such as rose oil, jasmine oil, black-currant oil or those of citrus-fruits such as orange, bergamot or lemon for example. Compound I may also be advantageously used for the preparation of perfumed products such as soaps, detergents, household materials or cosmetic preparations.

The proportions of compound I which are used to achieve an interesting olfactive effect may vary within a wide range, said proportions being however generally comprised between about 1 and about 10% (parts by weight) of the perfume composition. Depending on the desired effect, smaller quantities, for example of the order of 0.1%, or quantities as high as 20% may also be used. When compound I is used as reinforcing ingredient in base perfume compositions, quantities up to 80% may be used.

In the field of flavor industry 1-(5-methyl-fur-2-yl)-1-(5-methyl-5-vinyl-tetrahydrofur-2-yl)-ethane possesses an original, at one time green and fruity gustative note. Depending on the nature of the materials wherein it is incorporated or on the concentration used, compound I may advantageously enhance not only green and fruity notes but also various gustative notes such as woody or balsamic notes typical of the flavor and aroma of citrus-fruits for example. Compound I is therefore particularly suitable for the preparation of artificial flavors, those of black-currant, lemon or grapefruit in particular. Compound I is also appreciated for the aromatization of liquid or solid foodstuffs such as jams, jellies, syrups, dairy products, icecreams or even bakery and confectionery products. Compound I is also appreciated for the aromatization of pharmaceutical preparations or even tobacco products.

The term "foodstuff" is here used broadly and also includes products such as coffee, tea or chocolate.

When compound I is used for the aromatization of various foodstuffs, or beverages for example, the proportions used may vary within a wide range and mostly depend on the nature of the flavored material or on the effect desired. Interesting gustative effects such as those described above may be achieved by the use of proportions comprised between 1 ppm and 1% (parts by weight) of the flavored material, the most interesting effects being obtained by using quantities of the order of 50 to 100 ppm. When compound I is used as flavor ingredient for the preparation of artificial flavor compositions, the proportions used may be of the order of 0.1 to 15% of the given composition.

In all the above cases however, depending on the gustative or olfactive effects desired, smaller or higher proportions may also be used.

Due to the presence of several chirality centers in its molecule, namely at carbons 2 and 5 of the tetrahydrofuranic ring and the asymetrical carbon atom of the ethylidenic moiety, compound I can exist in the form of at least one of the following stereoisomers:

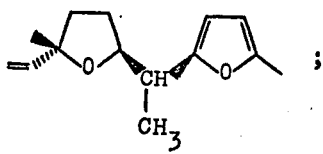

Ia

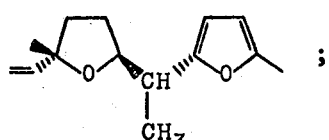

Ib

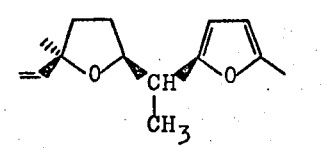

and

Ic

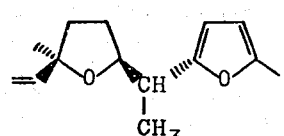

Id

In the present specification, formula I is deemed to represent either one individual stereoisomer or any mixture of at least two of the said stereoisomers.

Compounds Ia, Ib, Ic and Id have been separated each from the other by means of a careful vapor phase chromatography and individually characterized. However, for practical and economical reasons and for the utility disclosed in the present specification, compound I can be used in the form of an isomeric mixture.

As mentioned above, the first step of the process of the invention consists in condensing a ketone of formula

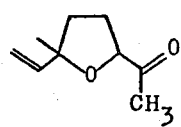

II with an organometallic derivative of furan of formula

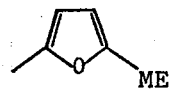

III wherein the symbol ME represents an alkali metal, for example Na, K or Li.

The above condensation may be carried out in accordance with the methods known in organic chemistry for the coupling reaction between a carbonyl compound and an organometallic derivative [see, e.g., A. P. Dunlop and F. N. Peters, The Furans, Reinhold Publ. New York 1953, p 254 and ff.].

According to a preferred embodiment of the present invention, compound II reacts with 5-methyl-fur-2-yl-lithium, in an inert organic solvent. Suitable organic solvents include an ether such as diethyl ether, tetrahydrofuran or dioxan. Anhydrous diethyl ether is preferably used [see J. Org. Chem. 27, 1216 (1967)].

The product resulting from the above condensation and subsequent hydrolysis is a tertiary alcohol of formula

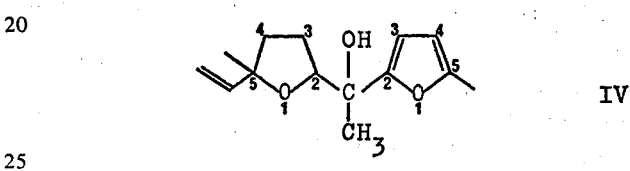

IV 1-(5-Methyl-fur-2-yl)-1(-5-methyl-5-vinyl-tetrahydrofuran-2-yl)-ethanol (IV), which is a new compound, can be isolated in its pure state and reduced then to compound I.

This particular reaction step however is not absolutely necessary for the good accomplishment of the process of the invention and the said reduction can also be carried out in situ, directly on the reaction mixture resulting from the above condensation.

The said reduction, which consists in fact in a hydrogenolysis, is effected by means of a mixture of aluminum trichloride and lithium-aluminum hydride, according to the method described in particular in J. Org. Chem. 29, 121 (1964). The presence of an inert organic solvent, for example an ether such as diethyl ether, dioxan or tetrahydrofuran is necessary. The same solvent as that used for the preceding condensation is preferred.

The organometallic derivative of formula III, used as starting material in the above process, can be obtained from the corresponding furanic compound in accordance with known methods [see, e.g., A. P. Dunlop and F. N. Peters, Op. cit. p. 193 and ff].

5-Methyl-5-vinyl-tetrahydrofur-2-yl-methyl ketone (II), also used as starting material in the above process, can be prepared from linalyl oxide, a commercially available compound, as illustrated hereinbelow:

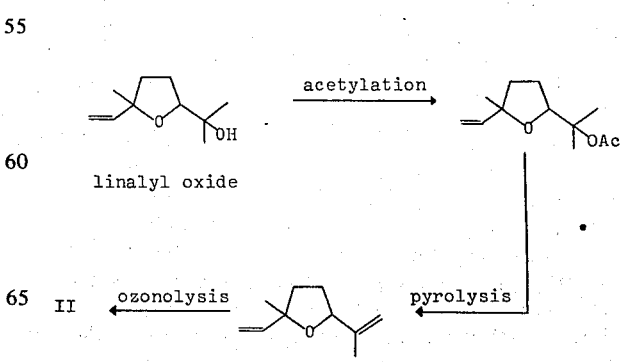

linalyl oxide

The acetylation of linalyl oxide is effected in accordance with the conventional techniques, for example by means of a pyridine-acetic anhydride mixture or by means of acetyl chloride in the presence of an organic base such as N,N-dimethylaniline.

The pyrolysis of the acetate thus obtained is carried out in accordance with known methods. For example, the said pyrolysis can be achieved as follows: a solution of the acetate in an inert solvent, n-hexane for example, is introduced dropwise at the top of a tube filled with glass helix and heated to a temperature of the order of 400°C.

The pyrolysate essentially consists of 2-isopropenyl-5-methyl-5-vinyl-tetrahydrofuran. This compound can also be prepared by a different method, by dehydrating linalyl oxide, for example by means of a pyridine-phosphorus oxychloride mixture.

The conversion of 2-isopropenyl-5-methyl-5-vinyl-tetrahydrofuran into compound II can be effected by an ozonolysis. This reaction is effected with conventional techniques [see, e.g., L. F. Fieser and M. Fieser, Reagents for Organic Chemistry, Vol I p 773, John Wiley & Sons, New York 1967], preferably at low temperature and in the presence of an organic or an aqueous organic solvent, ethyl acetate or methanol for example.

Compound II may exist as one of the two stereoisomers of formula

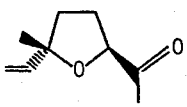 and 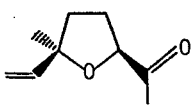

IIa                 IIb or as any mixture thereof.

When compound IIa reacts with 5-methyl-fur-2-yl-lithium, in accordance with a preferred embodiment of the process of the invention, compound I is isolated as a mixture of stereoisomers Ia and Ib. When compound IIb reacts in analogous conditions, a mixture of stereoisomers Ic and Id is then obtained. However, owing to the possibility of separating compounds Ia, Ib, Ic and Id each from the others — see above —, the stereoisomeric mixture IIa/IIb can also be conveniently used.

Finally, it was discovered that the acylated derivative of linalyl oxide as well as compound II also possessed useful organoleptic properties and that they can be advantageously used as perfuming and flavor-modifying ingredients.

The present invention will be better illustrated by the following Examples wherein the temperatures are given in degrees centigrade and the abbreviations have the meaning common in the art.

EXAMPLE 1

1-(5-Methyl-fur-2-yl)-1-(5-methyl-5-vinyl-tetrahydrofur-2-yl(-ethane — "two step process"

a. 110 ml of a 14% solution of butyl-lithium in hexane was added dropwise, under vigorous stirring and in a nitrogen atmosphere, to a cold (−35°) mixture of 12 g (0.14 Mole) of 2-methyl-furan, 24 ml of tetramethyl-ethylene-diamine and 150 ml of anhydrous diethyl. The obtained reaction mixture was then stirred for 3 hours, brought to −65° and 21 g (0.14 Mole) of 5-methyl-5-vinyl-tetrahydrofur-2-yl-methyl ketone — equimolecular mixture of stereoisomers IIa and IIb — were then rapidly added. The reaction mixture was stirred during 15 min. at −65°, then 1 hour at 0°, and finally poured onto 100 ml hydrochloric acid and 200 g of crushed ice. The organic layer was extracted twice with ether, neutralized, washed and dried over MgSO4. After evaporation and distillation of the obtained residue, there were isolated 35 g of a product having b.p 95°–100°/0.01 Torr and consisting essentially of 1-(5-methyl-fur-2-yl)-1-(5-methyl-5-vinyl-tetrahydrofur-2-yl)-ethanol.

An analytical sample was characterized by mass spectrometry.

MS: $M^+$ = 236 (2): m/e = 218 (8), 125 (100), 109 (13), 107 (18), 93 (13), 55 (15), 43 (52).

The thus obtained material can be used for the subsequent reaction step whithout any supplemental purification.

When cis-5-methyl-5-vinyl-tetrahydro-fur-2-yl-methyl ketone (IIb) was used as starting material in the above process, the corresponding carbinol was obtained as a mixture of two isomers (A and B), isolated in their pure state by a column chromatography (Silicagel - hexane/ether 5:1).

Isomer A

NMR: 1.23 (3H, s); 1.42 (3H, s); 1.6–2.1 (4H, m); 2.22 (3H, s); 4.14 (1H, d of t, J = 2, J' = 7 cps); 4.94 (1H, d of q, J = 2, J' = 10 cps); 5.09 (1H, d of q, J = 2, J' = 17 cps); 5.93 (1H, d of d, J = 10, J' = 17 cps); 5.80 and 6.02 (1H each, broad s) δ ppm.

Isomer B

NMR: 1.22 (3H, s); 1.32 (3H, s); 1.6–2.1 (4H, m); 2.2 (3H, s); 4.21 (1H, d of t, J = 2, J' = 7 cps); 4.90, 5.09, 5.92, 5.78 and 6.03: same attribution as above.

In analogous conditions, trans-5-methyl-5-vinyl-tetrahydrofur-2-yl-methyl ketone (IIa) also gave a mixture of isomers (C and D).

Isomer C

NMR: 1.21 (3H, s); 1.42 (3H, s); 1.5–2.1 (4H, m); 2.24 (3H, s); 4.07 (1H, d of t, J = 1, J' = 7 cps); 4.95 (1H, d of q, J = 2, J' = 10.5 cps); 5.15 (1H, d of q J = 2 J' = 17 cps); 5.83 (1H, d of d, J = 10.5 J' = 17 cps); 5.80 and 6.05 (1H each, broad s) δ ppm.

Isomer D

NMR: 1.22 (3H, s); 1.33 (3H, s); 1.5–2.0 (4H, m); 2.23 (3H, s); 4.16 (1H, t, J = 6.5 cps); 5.83 (1H, m); 4.92, 5.15, 5.80 and 6.04: same attribution as above.

b. 52.5 g of aluminum trichloride were progressively added to 200 ml of anhydrous diethyl ether, followed by 7.5 g of lithium-aluminum hydride. The above mixture was then cooled to 0° and 35 g of crude 1-(5-methyl-fur-2-yl)-1-(5-methyl-5-vinyl-tetrahydrofur-2-yl)-ethanol — see letter (a) — were then added dropwise, under vigourous stirring. 30 min. after addition of the reactants, the obtained mixture was poured onto crushed ice and the organic layer extracted with ether, washed with a saturated aqueous solution of NaHCO₃, then dried and evaporated in accordance with the usual techniques, to afford 28.9 g of raw material. The thus obtained residue was finally purified by means of a column chromatography (Silicagel - hexane/ether 9:1) followed by a fractional distillation, b.p. 49°–51°/0.001 Torr, of the eluate. 14.7 g (54%) of 1-(5-methyl-fur-2-yl)-1-(5-methyl-5-vinyl-tetra-hydrofur-2-yl-)-ethane were thus isolated, as a mixture of 4 isomers according to a vapor phase chromatography analysis (CARBOWAX 20 M - 5m — ca. 200°C.

NMR: 1.05–1.30 (6H, broad $s$); 1.45–1.90 (4H, $m$); 2.16 (3H, $s$); 2.50–3.10 (1H, $m$); 3.70–4.30 (1H, $m$); 4.75–5.30 (2H, $m$); 5.50–6.10 (3H, 2$m$) δ ppm ms: M$^+$ = 220 (4); m/e = 135 (6), 111 (19), 110 (10), 109 (100), 93 (15), 95 (9), 55 (15), 43 (28).

This isomeric mixture may be used according to the present invention without any further purification — see Examples 3 to 6.

For analytical reasons however, the aforementioned stereoisomers were separated by means of a vapour phase chromatography (CARBOWAX column) and individually characterized by NMR spectroscopy. The obtained results are given in the following table.

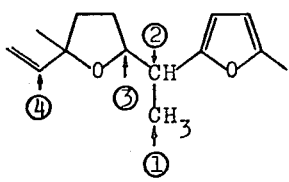

① to ④ define the NMR signals which were taken into consideration for the spectroscopic analysis.

| Attribution | | order of elution | | | |
|---|---|---|---|---|---|
| | | 4 | 3 | 2 | 1 |
| 1 | CH₃ (d) | 1.25 | 1.36 | 1.26 | 1.32 |
| 2 | H (m) | 3.05 | 2.90 | 3.09 | 2.91 |
| 3 | H (m) | 4.27 | 4.05 | 4.27 | 4.05 |
| 4 | H (d of d) | 5.96 | 5.95 | 5.91 | 5.89 |

EXAMPLE 2

1-(5-Methyl-fur-2-yl)-1-(5-methyl-5-vinyl-tetrahydrofur-2-yl)-ethane - "one step process"

595 g of a 14% solution of butyl-lithium in hexane were added over 2 hours at −10° to a mixture of 107 g (1.3 Mole) of 2-methylfuran and 800 ml of anhydrous ether as indicated above, in Example 1. The reaction mixture was heated to room temperature for 3 hours, then cooled at −10° and 200 g (1.3 Mole) of 5-methyl-5-vinyl-tetrahydrofuran-2-yl-methyl ketone (mixture of stereoisomers II$a$ and II$b$) were finally added. The obtained mixture was then kept overnight at a temperature of the order of −10° to −1°.

The above mixture was then added dropwise to a suspension of 433 g of aluminum trichloride and 9.12 g of lithium-aluminum hydride in 1600 ml of anhydrous ether. During the addition, the mixture was kept under stirring at 0° to 5° and finally stirred overnight at room temperature, after the addition of the reactants. The reaction mixture was then poured onto 2000 g of crushed ice and 3000 ml of water, extracted, dried and evaporated as indicated in Example 1. After distillation of the crude residue, there were obtained 137 g (48%) of 1-(5-methyl-fur-2-yl)-1-(5-methyl-5-vinyl-tetrahydrofur-2-yl)-ethane having b.p. 38°–60°/0.002 Torr.

5-Methyl-5-vinyl-tetrahydrofur-2-yl-methyl ketone, used as starting material in the above process, was prepared as follows:

i. 86.5 g of acetyl chloride and 51 g of acetic anhydride were added dropwise, under stirring, to a mixture of 170 g of linalyl oxide and 170 g of N,N-dimethylaniline. The reaction temperature, which was of the order of 5° to 10° at the beginning of the addition, finally reached 65°. The reaction mixture was then cooled to room temperature, poured onto a mixture of crushed ice and sulphuric acid and extracted with ether. After the usual treatments of washing, drying and distillation, there were isolated 201 g (95%), of the desired compound, b.p. 99°/10 Torr.

ms: m/e = 197 (1), 152 (6), 111 (38), 93 (23), 81 (11), 59 (18), 55 (25), 42 (100).

The above compound was isolated as a mixture of two isomeric acetates (A and B) which were separated by means of a vapor phase chromatography.

Isomer A

NMR: 1.25 (3H, $s$); 1.42 (6H, $s$); 1.91 (3H, $s$); 4.04 (1H, $m$); 4.75–5.40 (2H, $m$); 5.92 (1H, d of d, J = 10, J' = 17 cps) δ ppm.

Isomer B

NMR: 1.27 (3H, $s$); 1.43 (6H, $s$); 1.91 (3H, $s$); 4.00 (1H, $m$); 4.80–5.35 (2H, $m$); 5.83 (1H, d of d, J = 10 J' = 17 cps) δ ppm.

ii. a solution of 100 g of the above acetate in 500 ml of hexane was added dropwise at the top of a column (30 cm length) filled with glass helix and heated at 400°. The pyrolysate, which was collected in a NaHCO₃ aqueous solution, was extracted and finally purified as indicated sub letter (i), to afford 49 g (68%) of 2-isopropenyl-5-methyl-5-vinyl-tetrahydrofuran, in the form of an isomeric mixture (A and B).

MS: M$^+$ = 152 (2); m/e = 137 (19), 110 (25), 82 (38), 81 (25), 68 (84), 67 (100), 55 (90), 43 (65).

Isomers A and B were purified by means of a vapour phase chromatography, for analytical purpose only.

Isomer A

NMR: 1.27 (3H, $s$); 1.70 (3H, $s$); 4.30 (1H, $m$); 4.65–5.35 (4H, $m$); 5.92 (1H, d of d, J = 10, J' = 17 cps) δ ppm.

Isomer B

NMR: 1.28 (3H, $s$); 1.68 (3H, $s$), 4.31 (1H, $m$); 4.65–5.35 (4H, $m$); 5.86 (1H, d of d, J = 10, J' = 17 cps) δ ppm.

iii. a flow of ozone was passed through a cold (−70°) solution of 7.6 g of the isomeric mixture prepared sub letter ii) in 70 ml of ethyl acetate. After the absorbtion of 2.4 g of ozone, the reaction mixture was heated to −30° and 6.6 g of zinc powder were progressively added, followed by the addition of 13 ml of a 50% aqueous solution of acetic acid. The above mixture was then slowly heated to room temperature, stirred for 4 hours and finally filtered. After the usual treatments of extraction, washing and evaporation — see letter (i) —, there were isolated 2.7 g (36%) of 5-methyl-5-vinyl-tetrahydrofur-2-yl-methyl ketone having b.p. 72°–78°/10 Torr.

This compound was obtained as a mixture of isomers (A and B), which can be separated by means of a vapour phase chromatography.

Isomer A

NMR: 1.32 (3H, s); 2.21 (3H, s); 4.39 (1H, t, J = 7 cps); 5.02 (1H, d of d, J = 10.5, J' = 1.5 cps); 5.94 (1H, d of d, J = 10.5, J' = 18 cps) δ ppm.

MS: M+ = 154 (1); m/e = 139 (1), 111 (93), 93 (57), 81 (30), 69 (31), 67 (22), 43 (100).

Isomer B

NMR: 1.32 (3H, s); 2.15 (3H, s); 4.29 (1H, d of d, J = 6, J' = 8 cps); 4.95 (1H, d of d, J' = 10.5, J' = 1.5 cps); 5.10 (1H, d of d, J = 18, J' = 1.5 cps); 5.77 (1H, d of d, J = 10.5, J' = 18 cps) δ ppm.

MS: m/e = 125 (6), 111 (59), 93 (36), 81 (17), 69 (23), 67 (15), 55 (62), 43 (100).

EXAMPLE 3

A base perfume composition for a classical Eau de Cologne was prepared by mixing the following ingredients (parts by weight).

| | | |
|---|---|---|
| Synthetic lemon | 250 | |
| Synthetic bergamot | 300 | |
| Orange oil | 150 | |
| Petitgrain bigarade | 100 | |
| Neroli bigarade | 20 | |
| Lavender oil | 70 | |
| White thyme oil | 10 | |
| Cyclopentadecanolide 10 %* | 100 | |
| Total | 1000 | |

*in diethyl phthalate

By adding 10 g of 1-(5-methyl-fur-2-yl)-1-(5-methyl-5-vinyl-tetrahydrofur-2-yl)-ethane - isomeric mixture prepared in accordance with the process of Example 1 — to 90 g of the above base, there was obtained a new perfume composition possessing a fresh and fruity tonality, more powerful and more distinct than that of the said base. The thus obtained perfume composition possessed moreover an original olfactive note, reminiscent of that of lime.

EXAMPLE 4

A commercial bilberries jam was flavored with a 10% ethanolic (95% ethanol) solution of 1-(5-methyl-fur-2-yl)-1(5-methyl-5-vinyl-tetrahydrofur-2-yl)-ethane - isomeric mixture prepared in accordance with the process of Example 1 —, in the proportions of 10 ml of said ethanolic solution per 100 kg of flavoured material. The thus flavored foodstuff was then compared with an unflavoured jam containing 95% ethanol in the above given proportions. It was declared that the thus flavored jam possessed a fruity and woody note much more pronounced than that of the unflavored jam.

EXAMPLE 5

1 liter of a commercial grapefruit juice was flavored with 1 ml of a 1% ethanolic (95% ethanol) solution of 1-(5-methyl-fur-2-yl)-1-(5-methyl-5-vinyl-tetrahydrofur-2-yl) ethane — isomeric mixture prepared in accordance with the process of Example 1 —: "test" sample. A "control" sample was obtained by adding 1 ml of 95% ethanol to 1 liter of the above juice. The "test" and "control" beverages were then tested by a panel of experts who declared thaat the flavored juice ("test" sample) possessed an original fruity note, reminiscent of that of a fresh juice.

What is claimed is:

1. A pure compound of formula

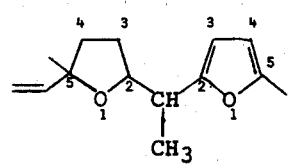

I

2. A pure compound selected from the group consisting of at least one compound of formula

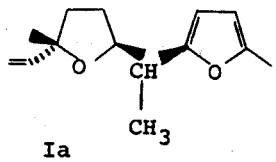

Ia

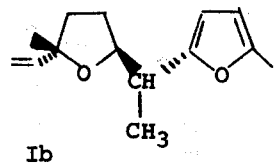

Ib

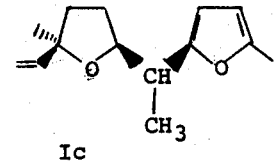 and

Ic

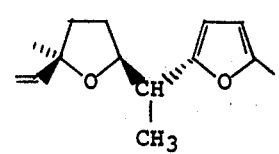

Id

* * * * *

UNITED STATES PATENT AND TRADEMARK OFFICE
CERTIFICATE OF CORRECTION

PATENT NO. : 3,931,250
DATED : January 6, 1976
INVENTOR(S) : Alan Francis Thomas It is certified that error appears in the above—identified patent and that said Letters Patent are hereby corrected as shown below:

Column 6, line 1, "anhydrous diethyl." should be --anhydrous diethyl ether.--

Column 10, line 14, "declared thaat" should be --declared that--.

Signed and Sealed this fourth Day of May 1976

[SEAL]

Attest:

RUTH C. MASON
*Attesting Officer*

C. MARSHALL DANN
*Commissioner of Patents and Trademarks*